United States Patent [19]

Thaxton, Sr.

[11] Patent Number: 5,346,483
[45] Date of Patent: Sep. 13, 1994

[54] EXTERNAL MALE CATHETER

[76] Inventor: Charles E. Thaxton, Sr., 325 Glen St., New Britain, Conn. 06051

[21] Appl. No.: 72,443

[22] Filed: Jun. 7, 1993

[51] Int. Cl.$^5$ .............................................. A61F 5/44
[52] U.S. Cl. ................... 604/353; 604/346; 604/347; 604/349; 604/351; 128/767
[58] Field of Search .................... 604/346–347, 604/349, 351, 353; 4/144.1–144.4; 128/760, 762, 767

[56] References Cited

U.S. PATENT DOCUMENTS

| | | | |
|---|---|---|---|
| 1,379,289 | 5/1921 | Rogers | 604/353 |
| 2,484,356 | 10/1949 | Ribeiro et al. | 604/353 |
| 2,494,477 | 1/1950 | Kurtz | 604/347 |
| 2,944,551 | 7/1960 | Breer | 604/347 |
| 3,721,243 | 3/1973 | Hesterman et al. | 604/353 |
| 4,022,213 | 5/1977 | Stein | 604/353 |
| 4,122,851 | 10/1978 | Grossner | 604/347 |
| 4,281,655 | 8/1981 | Terauchi | 604/347 |
| 4,387,726 | 6/1983 | Denard | 604/349 |
| 4,713,066 | 12/1987 | Komis | 604/349 |
| 4,713,067 | 12/1987 | Rothenberg et al. | 604/349 |
| 4,813,943 | 3/1989 | Smith | 604/353 |
| 4,820,291 | 4/1989 | Terauchi et al. | 604/349 |
| 4,840,625 | 6/1989 | Bell | 604/349 |
| 4,846,816 | 7/1989 | Manfredi | 604/349 |
| 4,886,508 | 12/1989 | Washington | 604/327 |
| 4,886,510 | 12/1989 | Matsuura | 604/349 |
| 4,892,527 | 1/1990 | Zivny | 604/349 |
| 4,997,427 | 3/1991 | Bowen | 604/349 |
| 5,009,649 | 4/1991 | Goulter et al. | 604/349 |
| 5,032,118 | 7/1991 | Mason | 604/349 |
| 5,147,341 | 9/1992 | Starke et al. | 604/349 |

FOREIGN PATENT DOCUMENTS

| | | | |
|---|---|---|---|
| 0657004 | 2/1963 | Canada | 604/349 |
| 0547044 | 3/1932 | Fed. Rep. of Germany | 604/349 |
| 0742099 | 11/1943 | Fed. Rep. of Germany | 604/349 |
| 0989974 | 9/1951 | France | 604/349 |
| 2422388 | 12/1979 | France | 604/349 |
| 0662725 | 10/1987 | Switzerland | 604/349 |
| 2223173 | 4/1990 | United Kingdom | 604/349 |

Primary Examiner—Randall L. Green
Assistant Examiner—P. Zuttarelli

[57] ABSTRACT

A new and improved external male catheter includes a waistband and a sheath support member attached to the waistband. A sheath member is attached to the sheath support member. The sheath support member includes a first aperture through which a penis is inserted into the sheath member. The sheath support member also includes a first attachment assembly positioned circumferentially around the aperture. A removable and replaceable sheath assembly includes a second attachment assembly which is complementary to the first attachment assembly and is attachable thereto. The sheath member includes a extension portion, located at one end of the sheath member. The extension portion includes a second aperture for draining urine from the sheath assembly. Straps, connected between the waistband and the sheath support member, stabilize the sheath support member with respect to the waistband. The waistband, the sheath support member, and the straps are sewn together to form a unified structure. A urine receptacle assembly, which includes a flexible bag containing a solid absorbent material, may be attached to the sheath support member by snap connectors. A urine conveying tubing is connected between the tubing connector and the extension portion of the sheath member. The urine conveying tubing conveys urine from the sheath member to the flexible bag member of the urine receptacle assembly. The closure assembly is comprised of a flexible, zipper-like closure. A heater assembly for heating the urine receptacle assembly may be provided.

12 Claims, 4 Drawing Sheets

EXTERNAL MALE CATHETER

BACKGROUND OF THE INVENTION

1. Field of the Invention

The present invention relates generally to catheters for collecting urine from male patients, and more particularly an externally worn male urinary catheter.

2. Description of the Prior Art

In a medical environment, the need to collect urine output from a patient is well known. For male patients, an invasive catheter may be used. The invasive catheter is inserted into the urinary tract through the penis. This procedure is sometimes very uncomfortable and even painful. In this respect, it would be desirable if a urine collecting device for a male were provided that did not require insertion of a catheter into the urinary tract in the penis.

Even in a non-medical environment, some males have bladder control problems. One solution to the bladder control problem is wearing an adult diaper. A number of disadvantages are associated with the use of an adult diaper. For one thing, they are generally suitable for only one use and are thereafter disposable. For this reason, they are quite expensive. Another disadvantage is that they are composed of materials that are effective heat insulators. For this reason, they are often uncomfortably hot to wear, especially on hot days. Furthermore, when they perform their designated function and collect released urine, the absorbed urine spreads by capillary action in the adult diaper exposing relatively large areas of the wearer's skin to urine. In this respect, it would be desirable if a urine collecting device for a male were provided which avoided the problems prevalent with the use of adult diapers.

A number of devices are disclosed in the U.S. patents for collecting urine from males without wearing an adult diaper. The following U.S. Pat. Nos. are representative: 3,559,651; 4,886,510; 4,963,137; 4,997,427; and 5,059,190.

More specifically, U.S. Pat. No. 3,559,651 discloses a body-worn disposable urinal that has an inner bag telescopically received in an outer bag. Both bags are attached to a collar which is attached directly to a waistband. A disadvantage of this device is that once urine passes from the inner bag to the outer bag, the urine essentially jackets the inner bag, and thereby jackets the penis. The urine has nowhere else to go. In this respect, it would be desirable if a urine collecting device for a male were provided that prevented the penis from being jacketed by released urine. Moreover, the direct connection between the waistband and the inner and outer bag assembly may prove to be uncomfortable. In its attachment to the bag assembly, the waistband may become uncomfortably tangled with pubic hair. In this respect, it would be desirable if a urine collecting device for a male were provided that avoids getting tangled with pubic hair.

U.S. Pat. No. 4,886,510 discloses a urine-collecting device designed to be used with a bedridden person. A penis is inserted directly into a urine-collecting bag, and the connection between the penis and the bag seems to be the only support for the bag on the body of the person. Such a device would not be practical for use with an ambulatory person. In this respect, it would be desirable if a urine collecting device for a male were provided which is suitable for use with an ambulatory person.

U.S. Pat. No. 4,963,137 discloses a device for urine drainage of a male. The device has a cup-like member which directly receives the front end of the penis. The cup-like member is secured to the front end of the penis, and the front end of the penis supports the entire weight of the device and the urine contents released into the device. Supporting the weight of the device and the weight of released urine by the front of the penis can be very uncomfortable. In this respect, it would be desirable if a urine collecting device for a male were provided whose weight and whose contents are not supported by the penis.

U.S. Pat. No. 5,059,190 discloses a device for urine drainage of a male. The device has an elongate cup member which directly receives the penis. The cup member is secured to the penis alone, and the penis supports the entire weight of the device and a drainage tube connected to the device. Supporting the weight of the device and drainage tube by the penis can be very uncomfortable. In this respect, it would be desirable if a urine collecting device for a male were provided whose weight whose drainage tube are not supported by the penis.

U.S. Pat. No. 4,997,427 discloses an external male urine collecting device that is worn by a person using a waistband and buttock straps. A cylindrical cup receives the penis, and a tube is connected to the tip of the cup for urine drainage. Although this device has advantages over the devices discussed above, a number of disadvantages are also noted. The device does not appear to be suitable for an ambulatory person. The urine is drained to a location extraneous to the wearer. In this respect, it would be desirable if a urine collecting device for a male were provided which provided for collection of released urine so that the device can be used with ambulatory persons. Another disadvantage with this device is that only one size penis-receiving cup is disclosed. In fact, sizes of male organs vary quite a bit in size from one person to another. In this respect, it would be desirable if a urine collecting device for a male were provided which is adaptable to males having different size male members. With this device, the cup for the penis is supported by the waistband and buttock straps, but the receiver for urine is not. For convenience, it would be desirable if a urine collecting device for a male were provided which contained a urine receiver supported by a waistband.

Once urine is released from the body, at body temperature, it begins to cool to ambient temperature. For a urine receiver that is in close proximity to the body, the feeling of the cooled urine can be quite uncomfortable, especially in cold weather. In this respect, it would be desirable if a urine collecting device for a male were provided which included means for warming urine released from the body.

When urine is received in a bag, it is in a liquid state. As such, it can slosh around, have its weight readily shift, and create undesirable sloshing sounds. In this respect, it would be desirable if a urine collecting device for a male were provided which included an absorbent material in the urine collecting bag to prevent emission of sloshing sounds from the received urine.

Thus, while the foregoing body of prior art indicates it to be well known to use devices to collect urine from males, the prior art described above does not teach or suggest an external male catheter which has the following combination of desirable features: (1) does not require insertion of a catheter into the urinary tract in the penis; (2) avoids the problems prevalent with the use of adult diapers; (3) prevents the penis from being jacketed by released urine; (4) avoids getting tangled with pubic hair; (5) is suitable for use with an ambulatory person; (6) its weight and its contents are not supported by the penis; (7) its weight and its drainage tube are not supported by the penis; (8) is adaptable to males having different size male members; (9) provides for collection of released urine so that the device can be used with ambulatory persons; (10) contains a urine receiver supported by a waistband; (11) includes means for warming urine released from the body; and (12) includes an absorbent material in the urine collecting bag to prevent emission of sloshing sounds from the received urine. The foregoing desired characteristics are provided by the unique external male catheter of the present invention as will be made apparent from the following description thereof. Other advantages of the present invention over the prior art also will be rendered evident.

SUMMARY OF THE INVENTION

To achieve the foregoing and other advantages, the present invention, briefly described, provides a new and improved external male catheter which includes a waistband and a sheath support member attached to the waistband. The sheath support member includes a first aperture through which a penis is inserted. The sheath support member also includes a first attachment assembly positioned circumferentially around the aperture. A removable and replaceable sheath assembly includes a second attachment assembly which is complementary to the first attachment assembly and is attachable thereto. The sheath assembly also includes a sheath member connected to the second attachment assembly. The sheath member receives the wearer's penis. The sheath member includes a extension portion, located at one end of the sheath member. The extension portion includes a second aperture for draining urine from the sheath assembly. The sheath support member is attached to the waistband by stitches. Straps, connected between the waistband and the sheath support member, stabilize the sheath support member with respect to the waistband. The straps are connected to the waistband and to the sheath support member by stitches. The waistband, the sheath support member, and the straps are connected together to form a unified structure.

A urine receptacle assembly may include a third attachment assembly capable of removable and replaceable attachment to a complementary fourth attachment assembly connected to the sheath support member, such that the urine receptacle assembly is supported by the sheath support member when the third attachment assembly and the fourth attachment assembly are connected together. The urine receptacle assembly includes a flexible bag member which includes a tubing connector. The flexible bag member includes a third aperture which permits the sheath member containing a penis to pass therethrough. The flexible bag member contains a quantity of solid urine absorbent material. The flexible bag member includes a closure assembly which, when opened, permits filling the flexible bag member with the solid absorbent material and permits emptying the solid absorbent material and absorbed urine from the flexible bag member.

A urine conveying tubing is connected between the tubing connector and the extension portion of the sheath member. The urine conveying tubing conveys urine from the sheath member to the flexible bag member of the urine receptacle assembly. The closure assembly is comprised of a flexible, zipper-like closure. The third attachment assembly and the fourth attachment assembly comprise a snap connector assembly.

A heater assembly for heating the urine receptacle assembly may be provided. The heater assembly includes a heating element assembly attached to and supported by the urine receptacle assembly. An electrical power source supplies an electrical conductor assembly with electrical energy. The electrical conductor assembly is connected between the heating element assembly and the electrical power source. The electrical energy from the electrical power source flows to the heating element assembly. The heating element assembly includes a fourth aperture which permits the sheath member to pass therethrough.

The electrical power source includes a plurality of rechargeable batteries, a housing for storing the rechargeable batteries, and an on/off switch for controlling flow of electricity into and out of the rechargeable batteries.

The above brief description sets forth rather broadly the more important features of the present invention in order that the detailed description thereof that follows may be better understood, and in order that the present contributions to the art may be better appreciated. There are, of course, additional features of the invention that will be described hereinafter and which will be for the subject matter of the claims appended hereto.

In this respect, before explaining at least three preferred embodiments of the invention in detail, it is understood that the invention is not limited in its application to the details of the construction and to the arrangements of the components set forth in the following description or illustrated in the drawings. The invention is capable of other embodiments and of being practiced and carried out in various ways. Also, it is to be understood, that the phraseology and terminology employed herein are for the purpose of description and should not be regarded as limiting.

As such, those skilled in the art will appreciate that the conception, upon which disclosure is based, may readily be utilized as a basis for designing other structures, methods, and systems for carrying out the several purposes of the present invention. It is important, therefore, that the claims be regarded as including such equivalent constructions insofar as they do not depart from the spirit and scope of the present invention.

Further, the purpose of the foregoing Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. Accordingly, the Abstract is neither intended to define the invention or the application, which only is measured by the claims, nor is it intended to be limiting as to the scope of the invention in any way.

It is therefore an object of the present invention to provide a new and improved external male urinary catheter which has all of the advantages of the prior art and none of the disadvantages.

It is another object of the present invention to provide a new and improved external male catheter which may be easily and efficiently manufactured and marketed.

It is a further object of the present invention to provide a new and improved external male urinary catheter which is of durable and reliable construction.

An even further object of the present invention is to provide a new and improved external male catheter which is susceptible of a low cost of manufacture with regard to both materials and labor, and which accordingly is then susceptible of low prices of sale to the consuming public, thereby making such external male urinary catheter apparatus available to the buying public.

Still yet a further object of the present invention is to provide a new and improved external male catheter which does not require insertion of a catheter into the urinary tract in the penis.

Still another object of the present invention is to provide a new and improved external male catheter apparatus that avoids the problems prevalent with the use of adult diapers.

Yet another object of the present invention is to provide a new and improved external male urinary catheter which prevents the penis from being jacketed by released urine.

Even another object of the present invention is to provide a new and improved external male urinary catheter apparatus that avoids getting tangled with pubic hair.

Still a further object of the present invention is to provide a new and improved external male catheter which is suitable for use with an ambulatory person.

Yet another object of the present invention is to provide a new and improved external male catheter apparatus wherein its weight and its contents are not supported by the penis.

Still another object of the present invention is to provide a new and improved external male catheter wherein its weight and its drainage tube are not supported by the penis.

Yet another object of the present invention is to provide a new and improved external male catheter apparatus that is adaptable to males having different size male members.

Still a further object of the present invention is to provide a new and improved external male urinary catheter that provides for collection of released urine so that the device can be used with ambulatory persons.

Yet another object of the present invention is to provide a new and improved external male catheter which contains a urine receiver supported by a waistband.

Still a further object of the present invention is to provide a new and improved external male catheter apparatus that includes means for warming urine released from the body.

Yet another object of the present invention is to provide a new and improved external male catheter which includes an absorbent material in the urine collecting bag to prevent emission of sloshing sounds from the received urine.

These together with still other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there are illustrated preferred embodiments of the invention.

BRIEF DESCRIPTION OF THE DRAWINGS

The invention will be better understood and the above objects as well as objects other than those set forth above will become more apparent after a study of the following detailed description thereof. Such description makes reference to the annexed drawing wherein.

DESCRIPTION OF THE PREFERRED EMBODIMENT

Figure 1:
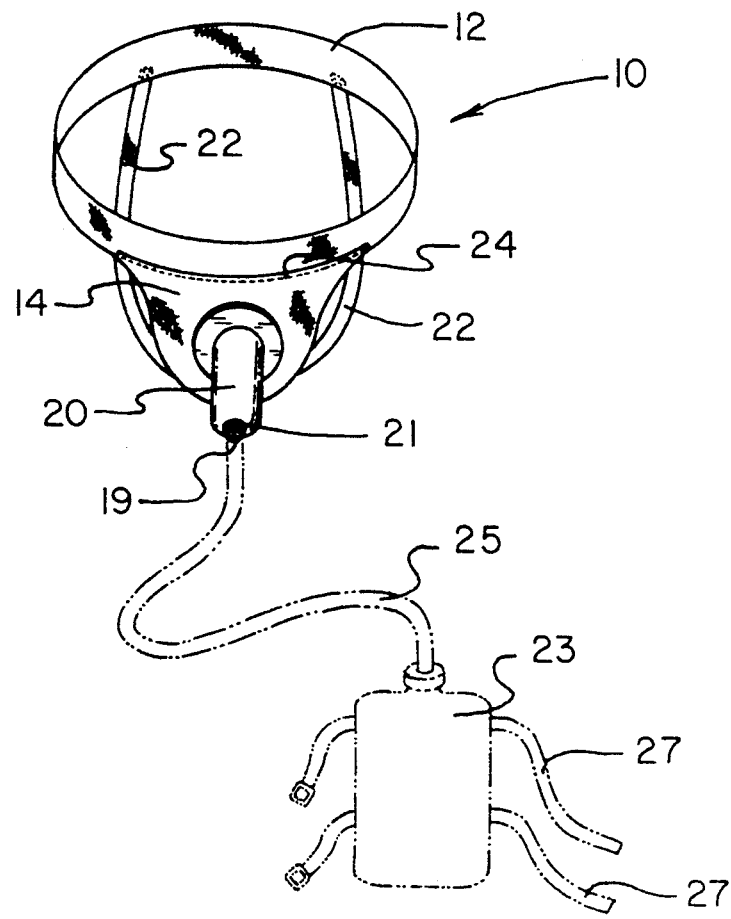
FIG. 1 is an elevated, frontal, perspective view showing a first preferred embodiment of the external male catheter of the invention used in conjunction with a standard leg bag for receiving urine drainage.
Figure 2:
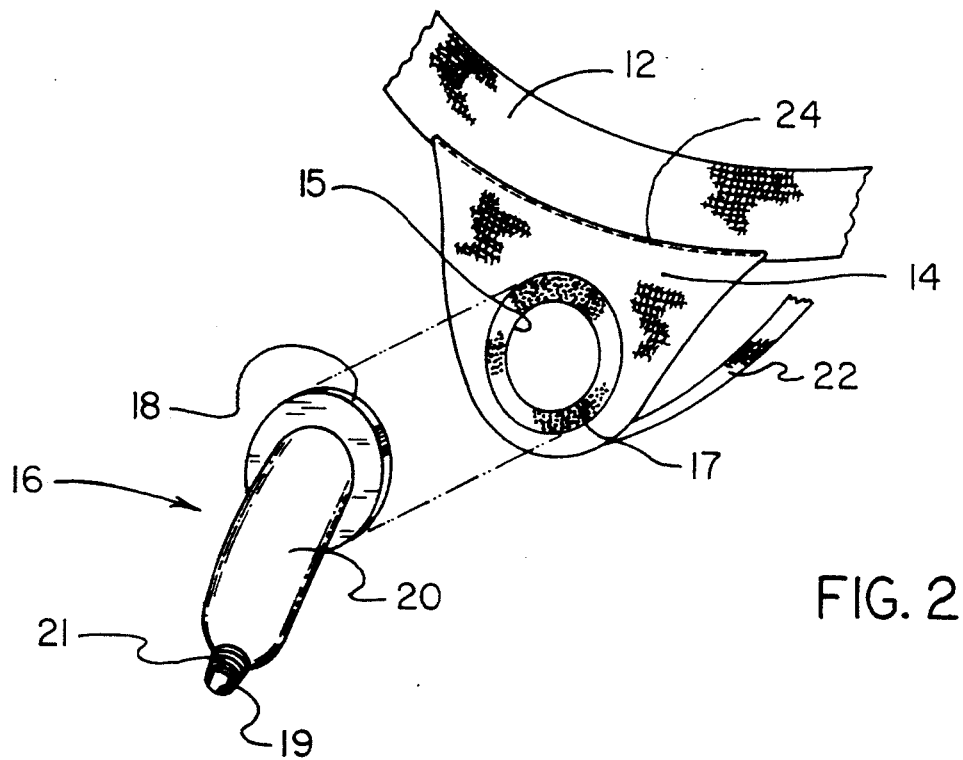
FIG. 2 is an enlarged, exploded view of sheath assembly of the embodiment shown in FIG. 1 separated from its sheath support member.
Figure 3:
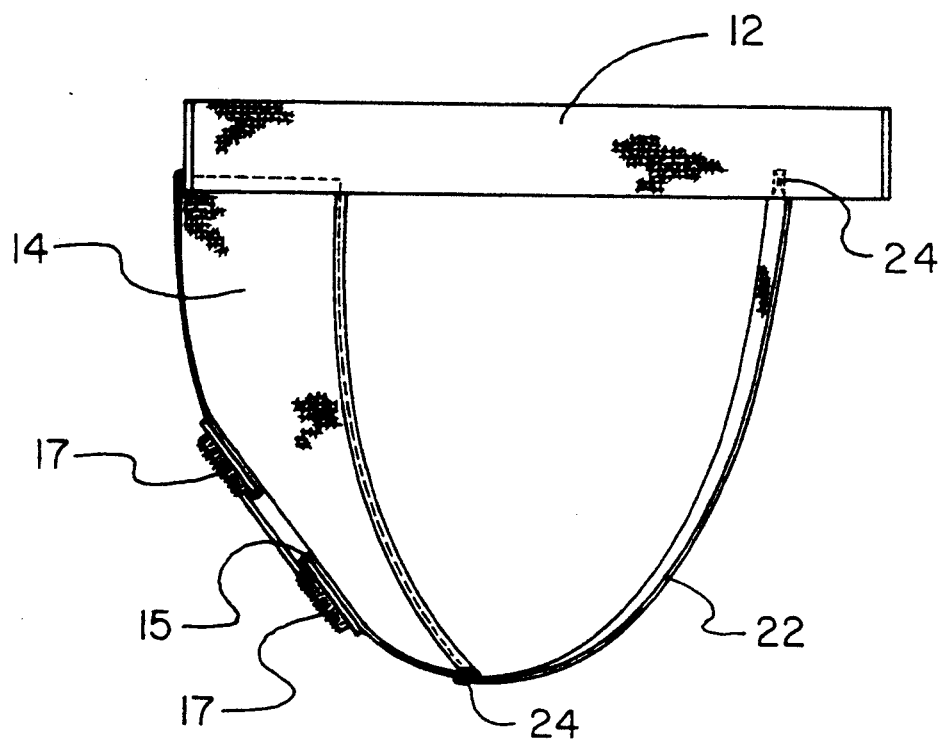
FIG. 3 is an enlarged side view of the embodiment shown in FIG. 1 with the sheath assembly removed.
Figure 4:
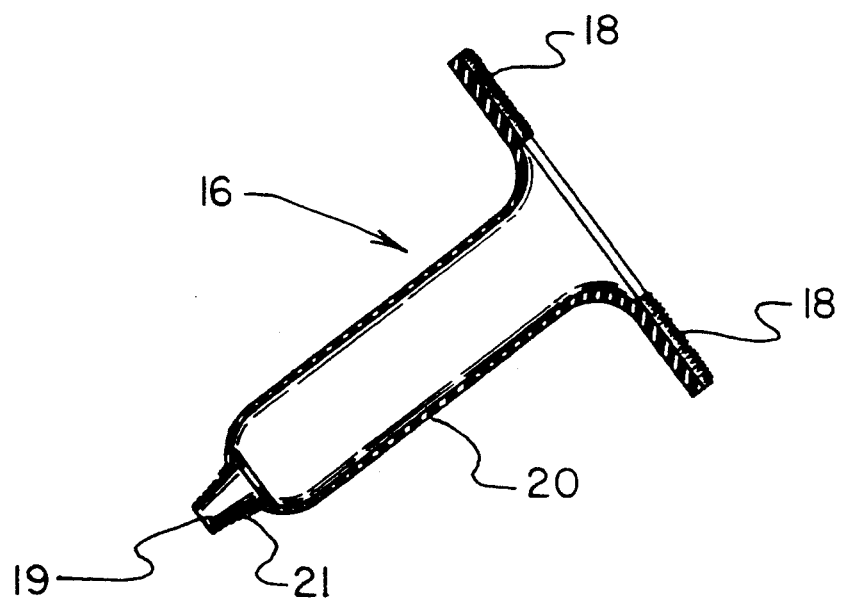
FIG. 4 is an enlarged cross-sectional side view of the sheath assembly shown in FIG. 1 without an accompanying sheath support member.

With reference to the drawings, a new and improved external male catheter embodying the principles and concepts of the present invention will be described.

Turning initially to FIGS. 1–4, there is shown a first exemplary embodiment of the external male catheter apparatus of the invention generally designated by reference numeral 10. In its preferred form, external male catheter 10 includes an elastic waistband 12 and a sheath support member 14 attached to the waistband 12. A sheath member 20 is supported by the sheath support member 14 and receives the penis. The sheath support member 14 includes a first aperture 15 through which the penis is inserted to be placed in the sheath member 20. The sheath support member 14 also includes a first attachment assembly 17 positioned circumferentially around the aperture 15. The sheath support member 14 can be made from a comfortable washable cloth material or one based on latex.

A removable and replaceable sheath assembly 16 includes a second attachment assembly 18 which is complementary to the first attachment assembly 17 and is attachable thereto. The sheath assembly 16 also includes the sheath member 20 connected to the second attachment assembly 18. The sheath member 20 includes a tapered extension portion 21, located at one end of the sheath member 20. The extension portion 21 includes a second aperture 19 for draining urine from the sheath assembly 16. The first attachment assembly 17 and the second attachment assembly 18 together are complementary hook and pile connector materials such as VELCRO(TM) material.

The extension portion 21 is connected to a conventional leg bag 23 through tubing 25. Straps 27 are used to secure the leg bag 23 to a leg of the wearer. The sheath members 20 can be provided in a variety of sizes to accommodate a variety of wearers. The sheath support member 14 is attached to the waistband 12 by stitches 24. Straps 22, connected between the waistband 12 and the sheath support member 14, stabilize the sheath support member 14 with respect to the waistband 12. Preferably, both the waistband 12 and the straps 22 are made of elastic material. The straps 22 are connected to the waistband 12 and to the sheath support member 14 by stitches 24. The waistband 12, the sheath support member 14, and the straps 22 are sewn together to form a unified structure.

Figure 5:
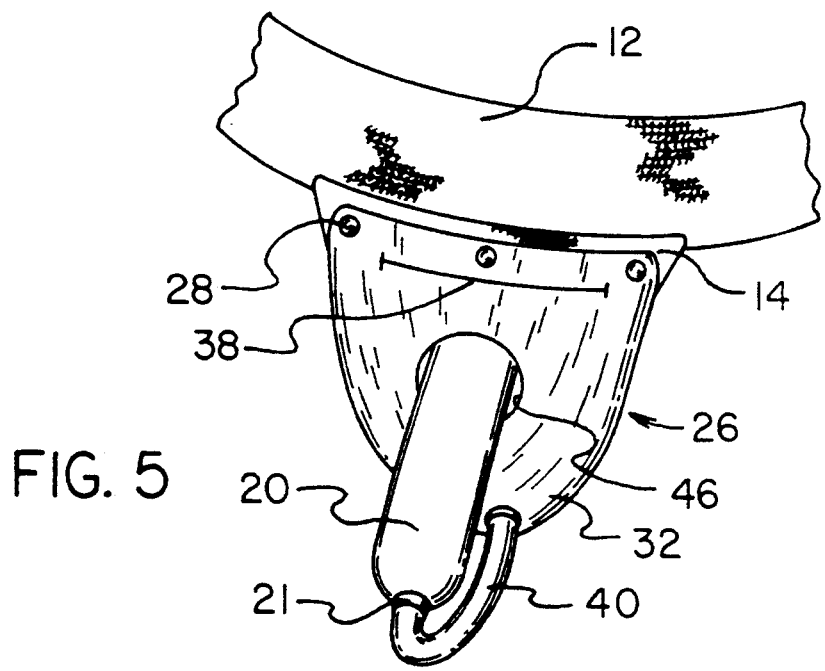
FIG. 5 is a partial, frontal perspective view in elevation of a second preferred embodiment of the invention of the external male catheter which includes a receiver for receiving urine drainage.
Figure 6:
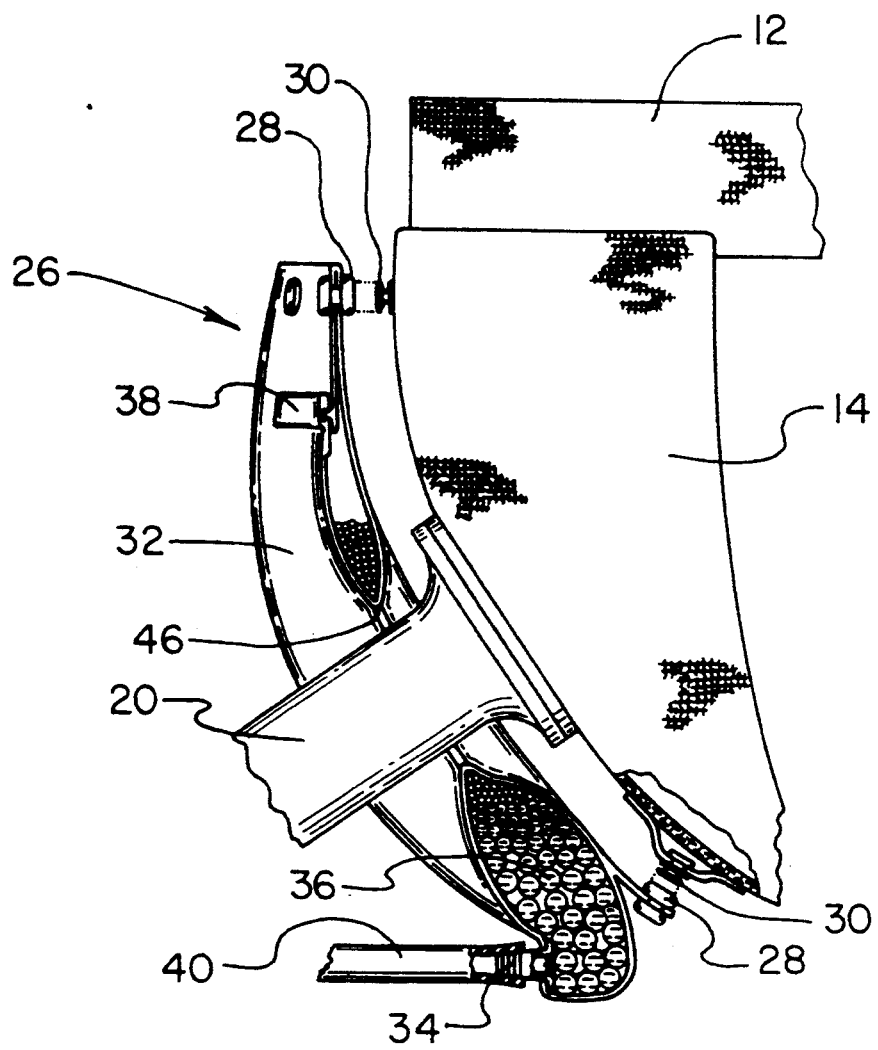
FIG. 6 is a partial, enlarged, exploded side view, partially in cross-section, of the embodiment shown in FIG. 5 wherein an absorbent material is shown inside the urine receiver.

Turning to FIGS. 5-6, a second embodiment of the invention is shown. Reference numerals are shown that correspond to like reference numerals that designate like elements shown in the other figures. In addition, a urine receptacle assembly 26 includes a third attachment assembly 28 capable of removable and replaceable attachment to a complementary fourth attachment assembly 30 connected to the sheath support member 14, such that the urine receptacle assembly 26 is supported by the sheath support member 14 when the third attachment assembly 28 and the fourth attachment assembly 30 are connected together.

The urine receptacle assembly 26 includes a flexible bag member 32 which includes a tubing connector 34. The flexible bag member 32 includes a third aperture 46 which permits the sheath member 20 containing a penis to pass therethrough. The flexible bag member 32 contains a quantity of solid urine absorbent material 36. The solid urine absorbent material 36 is preferably an inexpensive easily disposed of material such as activated charcoal, paper, raw cotton, or sawdust. Alternatively, absorbent microcapsules can be employed.

The flexible bag member 32 includes a closure assembly 38 which, when opened, permits filling the flexible bag member 32 with the solid absorbent material 36 and permits emptying the solid absorbent material 36 and absorbed urine from the flexible bag member 32. A urine conveying tubing 40 is connected between the tubing connector 34 and the extension portion 21 of the sheath member 20. The urine conveying tubing 40 conveys urine from the sheath member 20 to the flexible bag member 32 of the urine receptacle assembly 26. The closure assembly 38 is comprised of a flexible, zipper-like closure. The third attachment assembly 28 and the fourth attachment assembly 30 comprise a snap connector assembly.

Figure 7:
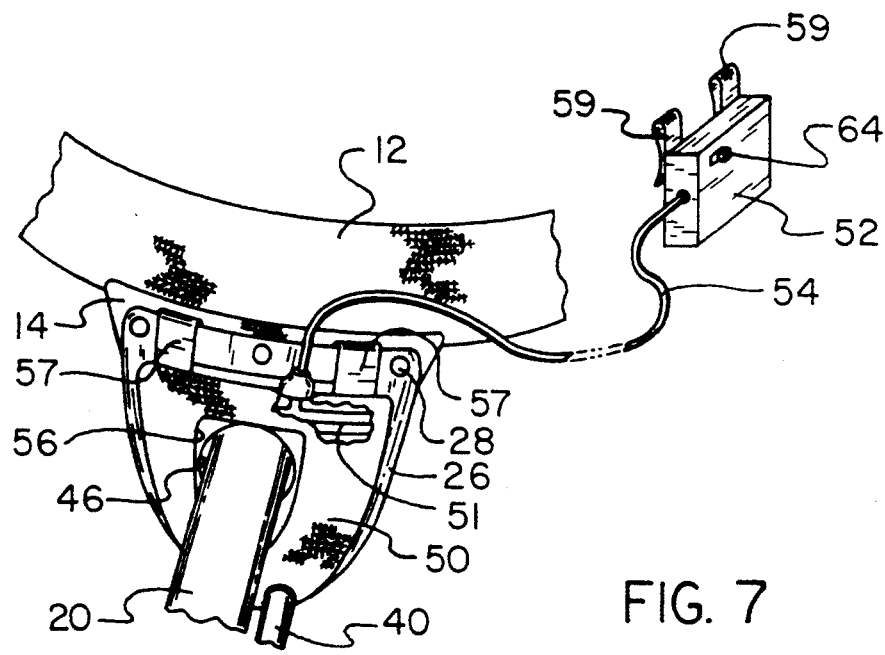
FIG. 7 is a partial, frontal perspective view in elevation of a third preferred embodiment of the invention of the external male catheter which includes a heating assembly, including rechargeable batteries, for heating urine received in the urine receiver.
Figure 8:
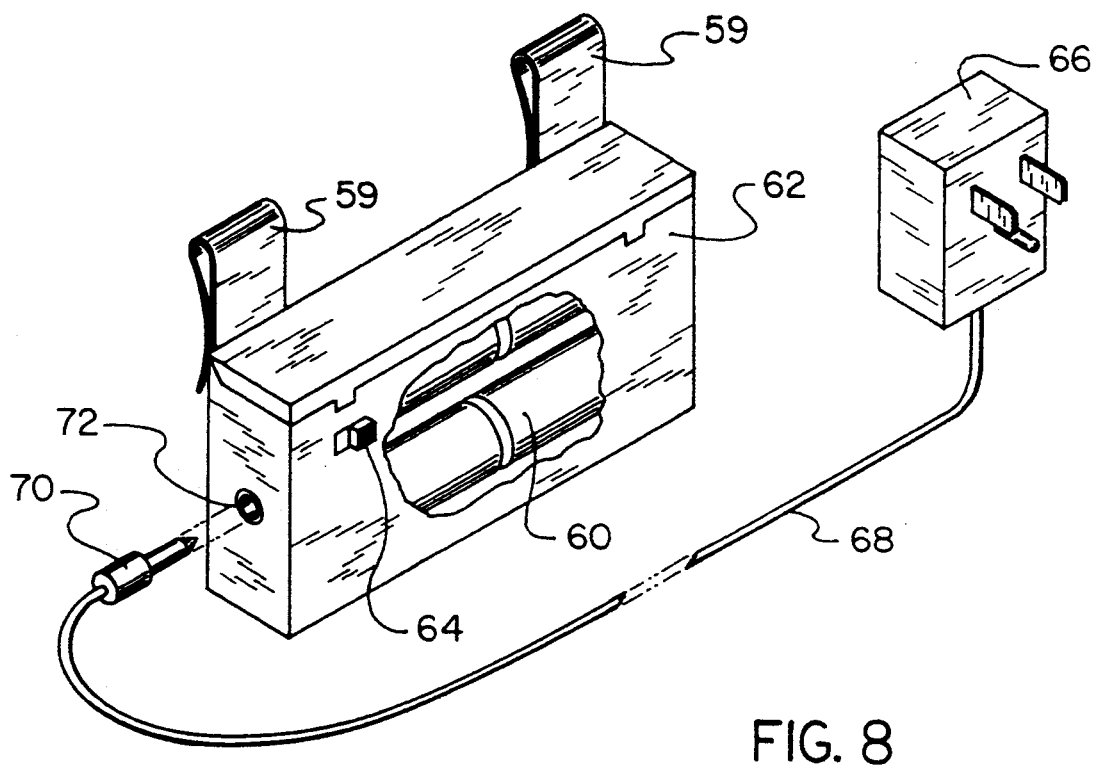
FIG. 8 is a perspective view a recharging assembly used to recharge the rechargeable batteries shown in FIG. 7.

Turning to FIGS. 7-8, a third embodiment of the invention is shown. Reference numerals are shown that correspond to like reference numerals that designate like elements shown in the other figures. In addition, a heater assembly for heating the urine receptacle assembly 26 is provided. The heater assembly includes a heating element assembly 50 attached to and supported by the urine receptacle assembly 26. The heating element assembly 50 includes a heating element 51. An electrical power source 52 supplies an electrical conductor assembly 54 with electrical energy. The electrical conductor assembly 54 is connected between the heating element assembly 50 and the electrical power source 52. The electrical energy from the electrical power source 52 flows to the heating element 51 in the heating element assembly 50. An ideal temperature to maintain for the urine receptacle assembly 26 by the heating element assembly 50 is body temperature. Clips 57 are used to connect the heating element assembly 50 to the urine receptacle assembly 26. In addition, clips 59 are used to connect the electrical power source 52 to a belt of a user. The heating element assembly 50 includes a fourth aperture 56 which permits the sheath member 20 to pass therethrough.

The electrical power source 52 includes a plurality of rechargeable batteries 60, a housing 62 for storing the rechargeable batteries 60, and an on/off switch 64 for controlling flow of electricity into and out of the rechargeable batteries 60. A combined transformer and AC to DC converter unit 66 is used to provide a recharging current to the rechargeable batteries 60 through electrical conductor assembly 68, plug 70, and jack 72.

Most of the components of the external male urinary catheter of the invention can be made from inexpensive and durable plastic, cloth, and rubberized materials.

It is apparent from the above that the present invention accomplishes all of the objects set forth by providing a new and improved external male catheter that is low in cost, relatively simple in design and operation, and which may advantageously be used so as not to require insertion of a catheter into the urinary tract in the penis. Also, with the invention, an external male urinary catheter apparatus is provided which avoids the problems prevalent with the use of adult diapers. With the invention, the penis is prevented from being jacketed by released urine. With the invention, pubic hair does not get tangled with the external male urinary catheter apparatus. With the invention, an external male urinary catheter is provided which is suitable for use with an ambulatory person. With the invention, an external male catheter is provided wherein its weight and its contents are not supported by the penis.

With the invention, an external male catheter is provided wherein its weight and its drainage tube are not supported by the penis. With the invention, an external male urinary catheter is provided which is adaptable to males having different size male members. With the invention, collection of released urine is provided so that the device can be used with ambulatory persons. With the invention, a urine receiver is supported by a waistband. With the invention, an external male catheter apparatus is provided which includes means for warming urine released frown the body. With the invention, an external male catheter is provided which includes an absorbent material in the urine collecting bag to prevent emission of sloshing sounds from the received urine.

With respect to the above description, it should be realized that the optimum dimensional relationships for the parts of the invention, to include variations in size, form function and manner of operation, assembly and use, are deemed readily apparent and obvious to those skilled in the art, and therefore, all relationships equivalent to those illustrated in the drawings and described in the specification are intended to be encompassed only by the scope of appended claims.

While the present invention has been shown in the drawings and fully described above with particularity and detail in connection with what is presently deemed to be the most practical and preferred embodiments of the invention, it will be apparent to those of ordinary skill in the art that many modifications thereof may be made without departing from the principles and concepts set forth herein. Hence, the proper scope of the present invention should be determined only by the broadest interpretation of the appended claims so as to encompass all such modifications and equivalents.

What is claimed as being new and desired to be protected by LETTERS PATENT of the United States is as follows:

1. A external male catheter, comprising:
   a waistband,
   a sheath support member attached to said waistband, said sheath support member including a first aperture through which a penis is inserted, said sheath support member also including a first attachment assembly positioned circumferentially around said aperture, and
   a removable and replaceable sheath assembly which includes a second attachment assembly which is complementary to said first attachment assembly and is attachable thereto, said sheath assembly also including a sheath member connected to said second attachment assembly, said sheath member including an extension portion, located at one end of said sheath member, said extension portion including a second aperture for draining urine from said sheath assembly,
   further including:
   a urine receptacle assembly in fluid communication with said sheath assembly including a third attachment assembly that can be removed and replaced for and replaceable attachment to a complementary fourth attachment assembly connected to said sheath support member, such that said urine receptacle assembly is supported by said sheath support member when said third attachment assembly and said fourth attachment assembly are connected together.

2. The apparatus described in claim 1 wherein said sheath support member is attached to said waistband by means of stitches.

3. The apparatus described in claim 1 wherein said third attachment assembly and said fourth attachment assembly comprise a snap connector assembly.

4. The apparatus described in claim 1, further including:
   straps, connected between said waistband and said sheath support member, for stabilizing said sheath support member with respect to said waistband.

5. The apparatus described in claim 4 wherein said straps are connected to said waistband and to said sheath support member by means of stitches.

6. The apparatus described in claim 4 wherein said waistband, said sheath support member, and said straps are connected together to form a unified structure.

7. The apparatus described in claim 1 wherein said urine receptacle assembly includes a flexible bag member which includes a tubing connector.

8. The apparatus described in claim 7 wherein said flexible bag member includes a third aperture which permits said sheath member to pass therethrough.

9. The apparatus described in claim 7 wherein said flexible bag member contains a quantity of solid urine absorbent material.

10. The apparatus described in claim 7, further including:
    a urine conveying tubing, connected between said tubing connector and said extension portion of said sheath member, for conveying urine from said sheath member to said flexible bag member of said urine receptacle assembly.

11. The apparatus described in claim 7 wherein said flexible bag member includes a closure assembly which, when opened, permits filling said flexible bag member with said solid absorbent material and permits emptying said solid absorbent material from said flexible bag member.

12. The apparatus described in claim 11 wherein said closure assembly is comprised of a flexible, zipper-like closure.

* * * * *